United States Patent
Ishikawa et al.

(10) Patent No.: US 8,664,413 B2
(45) Date of Patent: Mar. 4, 2014

(54) HIGH-PURITY EPOXY COMPOUND AND METHOD OF PRODUCING THEREOF

(75) Inventors: Michiya Ishikawa, Moriyama (JP); Hidetoshi Kato, Moriyama (JP); Jiro Nakatani, Moriyama (JP); Atsuhito Arai, Tacoma (JP); Hiroaki Sakata, Tacoma, WA (US); Hiroshi Taiko, Iyo-gun (JP)

(73) Assignee: Toray Fine Chemicals Co., Ltd. (JP)

( * ) Notice: Subject to any disclaimer, the term of this patent is extended or adjusted under 35 U.S.C. 154(b) by 0 days.

(21) Appl. No.: 13/636,153

(22) PCT Filed: Mar. 2, 2011

(86) PCT No.: PCT/JP2011/054806
§ 371 (c)(1),
(2), (4) Date: Sep. 20, 2012

(87) PCT Pub. No.: WO2011/118349
PCT Pub. Date: Sep. 29, 2011

(65) Prior Publication Data
US 2013/0012730 A1     Jan. 10, 2013

(30) Foreign Application Priority Data
Mar. 23, 2010 (JP) ................................ 2010-065378

(51) Int. Cl.
*C07D 301/24* (2006.01)
*C07D 303/08* (2006.01)

(52) U.S. Cl.
USPC ........................................ 549/520; 549/551

(58) Field of Classification Search
USPC .................................................. 549/520, 551
See application file for complete search history.

(56) References Cited

FOREIGN PATENT DOCUMENTS

| JP | 58-162584 A | 9/1983 |
|---|---|---|
| JP | 61-6828 | 1/1986 |
| JP | 63-54367 A | 3/1988 |
| JP | 2-169618 A | 6/1990 |
| JP | 3-26750 A | 2/1991 |
| JP | 4-225970 A | 8/1992 |
| JP | 04-335018 | 11/1992 |
| WO | 97/13745 | 4/1997 |
| WO | 2008/140008 A1 | 11/2008 |

OTHER PUBLICATIONS

Mustatâ, F. et al., "Multifunctional Epoxy Resins: Synthesis and Characterization," *Journal of Applied Polymer Science*, 2000, vol. 77, pp. 2430-2436.
Boutevin, B. et al., "Synthèse de Résines Époxydes Tétrafonctionnelles par L'Intermediaire de Diamines et de L'Épichlorhydrine," *European Polymer Journal*, 1995, vol. 31, No. 4, pp. 313-320.

*Primary Examiner* — Nizal Chandrakumar
(74) *Attorney, Agent, or Firm* — DLA Piper LLP (US)

(57) ABSTRACT

An epoxy compound of high-purity N,N,N',N'-tetraglycidyl-3,4'-diaminodiphenyl ether is produced by: an addition reaction step of reacting 3,4'-diaminodiphenyl ether with epichlorohydrin in a polar protic solvent at 65 to 100° C. for 12 hours or longer to form N,N,N',N'-tetrakis(3-chloro-2-hydroxypropyl)-3,4'-diaminodiphenyl ether; and a cyclization reaction step of reacting the N,N,N',N'-tetrakis(3-chloro-2-hydroxypropyl)-3,4'-diaminodiphenyl ether with an alkali compound for dehydrochlorination.

1 Claim, No Drawings

HIGH-PURITY EPOXY COMPOUND AND METHOD OF PRODUCING THEREOF

RELATED APPLICATIONS

This is a §371 of International Application No. PCT/JP2011/054806, with an international filing date of Mar. 2, 2011 (WO 2011/118349 A1, published Sep. 29, 2011), which is based on Japanese Patent Application No. 2010-065378, filed Mar. 23, 2010, the subject matter of which is incorporated by reference.

TECHNICAL FIELD

This disclosure relates to an industrially useful epoxy compound of high-purity N,N,N',N'-tetraglycidyl-3,4'-diaminodiphenyl ether, and to a method for producing the same.

BACKGROUND

Epoxy compounds are compounds widely used in the fields of organic chemistry and polymer chemistry. The compounds are useful in a variety of fields for industrial application, such as fine chemicals, raw materials of drugs, agrochemicals, and resins as well as electronic information materials and optical materials.

Further, when multi-functional epoxy compounds are cured with various hardeners, products thus cured are generally excellent in mechanical characteristics, water resistance, chemical resistance, heat resistance and electrical characteristics, and utilized in a broad range of fields as adhesives, paints, laminates, composite materials, and the like. In particular, glycidyl amine-type epoxy compounds are low in viscosity and excellent in heat resistance, and accordingly the usage thereof for composite materials and electronic materials is increased. Particularly, N,N,N',N'-tetraglycidyl-diaminodiphenyl ethers are useful raw materials for epoxy resins as fiber-reinforced composite materials (see, for example, Japanese Unexamined Patent Publication Kokai Nos. Hei 03-26750 and 04-335018). Epoxy compounds mainly containing N,N,N',N'-tetraglycidyl-diaminodiphenyl ethers are demanded to have a high purity for improving the performance of fiber-reinforced composite materials and also to have a low viscosity for suitable molding processability.

Conventionally, as a method for producing a glycidyl amine-type epoxy compound, there has been proposed a method in which a diamine is reacted with an epihalohydrin at a reaction temperature of less than 60° C. in the presence of 0.5 to 15 moles of water relative to 1 mole of the raw-material diamine (Japanese Examined Patent Publication No. Sho 61-6828). Moreover, as a method for producing N,N,N',N'-tetraglycidyl-4,4'-diaminodiphenyl ether, there has been proposed a method in which 4,4'-diaminodiphenyl ether is reacted with epichlorohydrin at a reaction temperature of 60° C. within a reaction period of 12 hours in a solvent of N,N-dimethylformamide or N,N-dimethylacetamide, which are polar aprotic solvents with a high boiling point (see, for example, Journal of Applied Polymer Science, Vol. 77, 2430-2436 (2000) and European Polymer Journal, Vol. 31, No. 4, pp. 313-320 (1995)). However, if that production method is employed for N,N,N',N'-tetraglycidyl-3,4'-diaminodiphenyl ether, resultant N,N,N',N'-tetraglycidyl-3,4'-diaminodiphenyl ether contains a large amount of impurities and has a high viscosity. This is attributable to a large difference between the reactivity of the amino group at the 3-position of raw-material 3,4'-diaminodiphenyl ether and the reactivity of the amino group at the 4-position of 4,4'-diaminodiphenyl ether.

Moreover, as a method for producing N,N,N',N'-tetraglycidyl-3,4'-diaminodiphenyl ether, it is stated that 3,4'-diaminodiphenyl ether is reacted with epichlorohydrin in a solvent mixture of benzene and acetic acid at a reaction temperature of 60° C. for 14 hours (International Patent Publication No. 97/13745). However, in that production method, when reacted with 3,4'-diaminodiphenyl ether, epichlorohydrin is simultaneously reacted with acetic acid. This brings about problems that a large amount of by-products are generated, and that N,N,N',N'-tetraglycidyl-3,4'-diaminodiphenyl ether thus obtained has a high viscosity.

In other words, when synthesized by the conventional methods, N,N,N',N'-tetraglycidyl-3,4'-diaminodiphenyl ether thus obtained contains a large amount of impurities in diglycidyl, triglycidyl, and chlorohydroxypropyl forms. These are highly reactive and react with the target product N,N,N',N'-tetraglycidyl-3,4'-diaminodiphenyl ether, bringing about a problem of lowering the quality. To put it differently, active hydrogens of the impurities in diglycidyl, triglycidyl, and chlorohydroxypropyl forms react with the target product N,N,N',N'-tetraglycidyl-3,4'-diaminodiphenyl ether, and gradually increase the viscosity. In addition, N,N,N',N'-tetraglycidyl-3,4'-diaminodiphenyl ether synthesized by the conventional methods contains a large amount of oligomers generated by reaction between an intermediate, N,N,N',N'-tetrakis(3-chloro-2-hydroxypropyl)-3,4'-diaminodiphenyl ether, formed in the production process and epichlorohydrin remaining in the system. This also causes the viscosity to be increased.

Particularly, when used as the raw material of an epoxy resin, N,N,N',N'-tetraglycidyl-3,4'-diaminodiphenyl ether with a high viscosity does not mix well with a hardener and an additive that are other components constituting the epoxy resin composition. This makes it difficult to obtain a uniform composition. Further, heating to obtain a uniform composition, however, results in disuniformity attributable to the aforementioned impurities in the diglycidyl, triglycidyl, and chlorohydroxypropyl forms. As a result, the resultant epoxy resin hardly has physical properties expected from the reaction between N,N,N',N'-tetraglycidyl-3,4'-diaminodiphenyl ether and the hardener.

Additionally, both of low-purity N,N,N',N'-tetraglycidyl-3,4'-diaminodiphenyl ether obtained by the conventional production methods and impurities contained therein have high boiling points. Accordingly, when the impurities are separated and removed by a method such as purification through distillation so as to increase the chemical purity, the distillation has to be performed at high temperature. This brings about a problem that the purity or the yield is lowered during the distillation. As described above, an industrially usable epoxy compound of high-purity N,N,N',N'-tetraglycidyl-3,4'-diaminodiphenyl ether has yet to be produced.

It could therefore be helpful to provide an epoxy compound of high-purity N,N,N',N'-tetraglycidyl-3,4'-diaminodiphenyl ether and a method for producing the same.

SUMMARY

Our high-purity epoxy compound is a high-purity epoxy compound of N,N,N',N'-tetraglycidyl-3,4'-diaminodiphenyl ether, and characterized in that the high-purity epoxy compound has a chemical purity of 85% or higher and has a viscosity at 40° C. of 40 Pa·s or lower measured using an E-type viscometer.

A method for producing a high-purity epoxy compound is characterized by including: an addition reaction step of reacting 3,4'-diaminodiphenyl ether with epichlorohydrin in a polar protic solvent at 65 to 100° C. for 12 hours or longer to form N,N,N',N'-tetrakis(3-chloro-2-hydroxypropyl)-3,4'-diaminodiphenyl ether; and a cyclization reaction step of reacting N,N,N',N'-tetrakis(3-chloro-2-hydroxypropyl)-3,4'-diaminodiphenyl ether thus obtained with an alkali compound for dehydrochlorination, whereby N,N,N',N'-tetraglycidyl-3,4'-diaminodiphenyl ether is produced.

According to our high-purity epoxy compound, N,N,N',N'-tetraglycidyl-3,4'-diaminodiphenyl ether can have a high chemical purity of 85% or higher, and also have a viscosity at 40° C. of 40 Pa·s or lower measured using an E-type viscometer.

According to our method for producing a high-purity epoxy compound, the production process is separated into: an addition reaction step of reacting 3,4'-diaminodiphenyl ether with epichlorohydrin in a polar protic solvent at 65 to 100° C. for 12 hours or longer to form N,N,N',N'-tetrakis(3-chloro-2-hydroxypropyl)-3,4'-diaminodiphenyl ether that is a tetrafunctional product of 3-chloro-2-hydroxypropyl; and a cyclization reaction step for dehydrochlorinating the chlorohydroxypropyl product thus obtained. Accordingly, it is possible to efficiently produce the epoxy compound in which N,N,N',N'-tetraglycidyl-3,4'-diaminodiphenyl ether has a chemical purity of 85% or higher and has a viscosity at 40° C. of 40 Pa·s or lower measured using an E-type viscometer. Moreover, since N,N,N',N'-tetraglycidyl-3,4'-diaminodiphenyl ether has a high purity, a purification step can be omitted, and no purification step is necessary. In other words, a purification step thus omitted never lowers the yield.

According to this production method, N,N,N',N'-tetraglycidyl-3,4'-diaminodiphenyl ether having a chemical purity of 85% or higher and a viscosity at 40° C. of 40 Pa·s or lower with an E-type viscometer can be produced.

Moreover, as the polar protic solvent used in the addition reaction step is at least one solvent selected from water and alcohols having 2 or more carbon atoms, generation of by-products is suppressed, the chemical purity of N,N,N',N'-tetraglycidyl-3,4'-diaminodiphenyl ether can be further increased.

Moreover, the reaction in the cyclization reaction step is preferably carried out in the presence of a quaternary ammonium salt and/or a quaternary phosphonium salt. Accordingly, N,N,N',N'-tetraglycidyl-3,4'-diaminodiphenyl ether can be produced efficiently, and the chemical purity thereof can be further increased while the viscosity thereof can be lowered.

Further, as at least one solvent selected from a hydrocarbon solvent, a halogenated hydrocarbon solvent, an ether solvent, an ester solvent, a ketone solvent, a nitrogen compound solvent, and a sulfur compound solvent is used in addition to the polar protic solvent in the addition reaction step, generation of by-products is suppressed, and the chemical purity of N,N,N',N'-tetraglycidyl-3,4'-diaminodiphenyl ether can be further increased, while the viscosity thereof can be lowered.

Additionally, as described above, the high-purity epoxy compound has a high chemical purity and a low impurity content, and accordingly is excellent in thermal stability. Thus, even if the production is carried out in larger-scale reactions, an epoxy compound having a chemical purity of 85% or higher and a viscosity at 40° C. of 40 Pa·s or lower with an E-type viscometer is stably obtained.

DETAILED DESCRIPTION

Hereinafter, a high-purity epoxy compound and a method for producing the high-purity epoxy compound will be described in detail.

The high-purity epoxy compound is N,N,N',N'-tetraglycidyl-3,4'-diaminodiphenyl ether having a chemical purity of 85% or higher and a viscosity at 40° C. of 40 Pa·s or lower measured using an E-type viscometer. In the epoxy compound, the chemical purity of N,N,N',N'-tetraglycidyl-3,4'-diaminodiphenyl ether is 85% or higher, preferably 90 to 100%, and more preferably 92 to 100%. Since the chemical purity of N,N,N',N'-tetraglycidyl-3,4'-diaminodiphenyl ether is quite high, excellent properties can be obtained when the epoxy compound is used as the main agent of an epoxy resin composition. Note that the chemical purity refers to a content of N,N,N',N'-tetraglycidyl-3,4'-diaminodiphenyl ether in the epoxy compound, and is analyzed (in HPLC area %) by a high-performance liquid chromatography method under the following analysis conditions:

Column: YMC-Pack ODS-AM303, 4.60×250 mm
Column temperature: 40° C.
Mobile phase: aqueous solution of methanol:0.1% (v/v) phosphoric acid=60:40 (v/v)
Flow rate=1 ml/min
Injected amount: 3 μl
Detection: UV at 254 nm
Analysis period: 90 minutes
Analysis sample preparation: 0.02 g of a sample was weighed, and diluted into approximately 40 ml of ethylene glycol dimethyl ether.

The epoxy compound has a low viscosity at 40° C. of 40 Pa·s or lower measured using an E-type viscometer. This can make favorable handling properties and molding processability of the epoxy resin composition before curing. The viscosity of the epoxy compound is a viscosity at 40° C. measured using an E-type viscometer, and is preferably 35 Pa·s or lower. The viscosity of the epoxy compound within such a range can make the epoxy resin composition containing this be a uniform composition easily, and also make favorable handling properties and molding processability of the epoxy resin composition. Moreover, as described above, the epoxy compound has a high chemical purity and a low impurity content, and accordingly is excellent in storage stability, and the viscosity rarely increases over time. Note that the viscosity of the epoxy compound is measured by using an E-type viscometer with the following method:

Viscometer: RE80U (manufactured by Toki Sangyo Co., Ltd.), rotor code No. 1
Temperature: 40° C.
Rotation speed: 1 rpm.

The method for producing a high-purity epoxy compound is carried out in two steps: an addition reaction step of reacting 3,4'-diaminodiphenyl ether with epichlorohydrin in a polar protic solvent at 65 to 100° C. for 12 hours or longer to form N,N,N',N'-tetrakis(3-chloro-2-hydroxypropyl)-3,4'-diaminodiphenyl ether; and a cyclization reaction step of reacting N,N,N',N'-tetrakis(3-chloro-2-hydroxypropyl)-3,4'-diaminodiphenyl ether obtained in the addition reaction step with an alkali compound for dehydrochlorination, the cyclization reaction step proceeding after completion of the addition reaction step.

Specifically, in the addition reaction step, four molecules of epichlorohydrin are added to one molecule of 3,4'-diaminodiphenyl ether in the polar protic solvent, and thereby N,N,N',N'-tetrakis(3-chloro-2-hydroxypropyl)-3,4'-diaminodiphenyl ether is formed. In the cyclization reaction step subsequent to this, N,N,N',N'-tetrakis(3-chloro-2-hydroxypropyl)-3,4'-diaminodiphenyl ether is dehydrochlorinated by the alkali compound, and thereby a tetrafunctional epoxy form, N,N,N',N'-tetraglycidyl-3,4'-diaminodiphenyl ether, is formed.

In the addition reaction step, the amount of epichlorohydrin used is preferably 5 to 40-fold by mole, more preferably 8 to 20-fold by mole, relative to one mole of 3,4'-diaminodiphenyl ether. If the amount of epichlorohydrin used is less than 5-fold by mole, impurities such as diglycidyl, triglycidyl, and oligomer forms are increased, and the purity and yield of N,N,N',N'-tetrakis(3-chloro-2-hydroxypropyl)-3,4'-diaminodiphenyl ether targeted in the addition reaction step are lowered. Meanwhile, if the amount of epichlorohydrin used exceeds 40-fold by mole, a large amount of energy is required to separate the target from the reaction liquid containing unreacted epichlorohydrin after the addition reaction step, and also a larger amount of waste is generated. Thus, such an amount is economically disadvantageous.

In the addition reaction step, the polar protic solvent is used as the reaction solvent. In conventional production methods described in Journal of Applied Polymer Science, Vol. 77, 2430-2436 (2000) and European Polymer Journal, Vol. 31, No. 4, pp. 313-320 (1995), polar aprotic solvents such as N,N-dimethylformamide and N,N-dimethylacetamide are used as the reaction solvent. However, use of such polar aprotic solvents is likely to cause an addition reaction of epichlorohydrin to a hydroxyl group of a chlorohydroxypropyl product thus formed. In contrast, in a case where the polar protic solvent is used as the reaction solvent, the reaction between a chlorohydroxypropyl product and epichlorohydrin can be suppressed. This suppresses generation of impurities, and can increase the chemical purity, while lowering the viscosity.

Examples of the polar protic solvent include water, alcohols, and phenols. Particularly, water and alcohols having 2 or more carbon atoms are preferable. Note that the polar protic solvent used in the present invention does not contain a carboxylic acid. If the polar protic solvent contains a carboxylic acid, problems are brought about: a side reaction occurs between the carboxylic acid and epichlorohydrin, a large amount of by-products are generated, the purity is lowered, and the viscosity is increased. Herein, examples of the carboxylic acid include formic acid, acetic acid, propionic acid, butyric acid, valeric acid, caproic acid, enanthic acid, caprylic acid, pelargonic acid, capric acid, lauric acid, myristic acid, palmitic acid, margaric acid, stearic acid, oleic acid, linoleic acid, linolenic acid, oxalic acid, malonic acid, succinic acid, glutaric acid, adipic acid, fumaric acid, maleic acid, benzoic acid, phthalic acid, salicylic acid, and the like.

The water is not particularly limited, and generally-available industrial water can be used. Specifically, the water may be river water, groundwater, lake water, seawater, brine water, and the like which are the water source and purified by precipitation, coagulation, filtration, distillation, ion exchange, ultrafiltration, reverse osmosis, or the like.

The alcohols include monofunctional alcohols and polyhydric alcohols. Examples thereof include primary alcohols such as methanol, ethanol, 1-propanol, 1-butanol, 1-pentanol and 1-hexanol; secondary alcohols such as isopropanol, 2-butanol, 2-pentanol, 3-pentanol, 2-hexanol, cyclohexanol, 2-heptanol and 3-heptanol; tert-butanol, tert-pentanol, ethylene glycol, ethylene glycol monomethyl ether, ethylene glycol monoethyl ether, ethylene glycol mono-n-propyl ether, ethylene glycol mono-n-butyl ether, ethylene glycol monophenyl ether, diethylene glycol, diethylene glycol monomethyl ether, diethylene glycol monoethyl ether, diethylene glycol mono-n-propyl ether, diethylene glycol mono-n-butyl ether, triethylene glycol, triethylene glycol monomethyl ether, triethylene glycol mono-n-butyl ether, propylene glycol, propylene glycol monomethyl ether, propylene glycol monoethyl ether, propylene glycol mono-n-propyl ether, propylene glycol mono-n-butyl ether, propylene glycol monophenyl ether, dipropylene glycol, dipropylene glycol monomethyl ether, dipropylene glycol monoethyl ether, dipropylene glycol mono-n-propyl ether, dipropylene glycol mono-n-butyl ether, tripropylene glycol, tripropylene glycol monomethyl ether, tripropylene glycol mono-n-butyl ether, and the like. Above all, alcohols having 2 or more carbon atoms are preferable, which can suppress the reaction between the chlorohydroxypropyl product and epichlorohydrin while not inhibiting the reaction of epichlorohydrin to 3,4'-diaminodiphenyl ether. Examples of the alcohols having 2 or more carbon atoms include ethanol, 1-propanol, isopropanol, 1-butanol, 2-butanol, 1-pentanol, 2-pentanol, 3-pentanol, tert-butanol, and tert-pentanol.

Examples of the phenols include phenol, cresol, o-cresol, m-cresol, p-cresol, and xylenol. The polar protic solvent used in the addition reaction step may be used alone or in combination of two or more kinds.

The amount of the polar protic solvent used is preferably 0.05 to 40-fold by weight, more preferably 0.1 to 20-fold by weight, of 3,4'-diaminodiphenyl ether. When the amount of the polar protic solvent used is within such a range, the reaction between the chlorohydroxypropyl product and epichlorohydrin can be suppressed.

In the addition reaction step, a solvent other than the polar protic solvent may also be present, as long as the reaction between 3,4'-diaminodiphenyl ether and epichlorohydrin is not inhibited. Examples of the solvent other than the polar protic solvent include a hydrocarbon solvent, a halogenated hydrocarbon solvent, an ether solvent, an ester solvent, a ketone solvent, a nitrogen compound solvent, and a sulfur compound solvent.

Examples of the hydrocarbon solvent include hexane, 2-methylpentane, 2,2-dimethylbutane, 2,3-dimethylbutane, heptane, octane, isooctane, nonane, trimethylhexane, decane, dodecane, benzene, toluene, xylene, ethylbenzene, cumene, mesitylene, cyclohexylbenzene, diethylbenzene, cyclopentane, methylcyclopentane, cyclohexane, methylcyclohexane, ethylcyclohexane, and the like. Above all, toluene is preferable.

Examples of the halogenated hydrocarbon solvent include methyl chloride, dichloromethane, chloroform, carbon tetrachloride, ethyl chloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, propyl chloride, isopropyl chloride, 1,2-dichloropropane, 1,2,3-trichloropropane, butyl chloride, sec-butyl chloride, isobutyl chloride, tert-butyl chloride, 1-chloropentane, chlorobenzene, o-dichlorobenzene, m-dichlorobenzene, p-dichlorobenzene, 1,2,4-trichlorobenzene, o-chlorotoluene, p-chlorotoluene, 1-chloronaphthalene, chlorinated naphthalene, methyl bromide, bromoform, ethyl bromide, 1,2-dibromoethane, 1,1,2,2-tetrabromoethane, propyl bromide, isopropyl bromide, bromobenzene, o-dibromobenzene, 1-bromonaphthalene, fluorobenzene, benzotrifluoride, hexafluorobenzene, chlorobromomethane, trichlorofluoromethane, 1-bromo-2-chloroethane, 1,1,2-trichloro-1,2,2-trifluoroethane, 1,1,2,2-tetrachloro-1,2-difluoroethane, and the like.

Examples of the ether solvent include diisopropyl ether, dibutyl ether, dihexyl ether, anisole, phenetole, diphenyl ether, dioxane, trioxane, tetrahydrofuran, tetrahydropyran, ethylene glycol dibutyl ether, diethylene glycol dimethyl ether, diethylene glycol diethyl ether, diethylene glycol dibutyl ether, and the like.

Examples of the ester solvent include methyl formate, ethyl formate, propyl formate, butyl formate, isobutyl formate, pentyl formate, methyl acetate, ethyl acetate, propyl acetate, isopropyl acetate, butyl acetate, isobutyl acetate, sec-butyl acetate, pentyl acetate, isopentyl acetate, 3-methoxybutyl acetate, sec-hexyl acetate, 2-ethylbutyl acetate, 2-ethylhexyl acetate, cyclohexyl acetate, benzyl acetate, methyl propionate, ethyl propionate, butyl propionate, isopentyl propionate, butyric acid ester, isobutyric acid ester, isovaleric acid ester, stearic acid ester, benzoic acid ester, ethylene glycol monoacetate, ethylene diacetate, ethylene glycol ester, diethyl carbonate, and the like.

Examples of the ketone solvent include acetone, 2-butanone, 2-pentanone, 3-pentanone, 2-hexanone, methyl isobutyl ketone, 2-heptanone, 4-heptanone, diisobutyl ketone, acetonylacetone, cyclohexanone, methylcyclohexanone, and acetophenone.

Examples of the nitrogen compound solvent include nitromethane, nitroethane, 1-nitropropane, 2-nitropropane, nitrobenzene, acetonitrile, propionitrile, succinonitrile, butyronitrile, isobutyronitrile, valeronitrile, benzonitrile, α-tolunitrile, pyridine, α-picoline, β-picoline, γ-picoline, 2,4-lutidine, 2,6-lutidine, quinoline, isoquinoline, N,N-dimethylformamide, N,N-diethylformamide, N,N-dimethylacetamide, and the like.

Examples of the sulfur compound solvent include carbon disulfide, dimethyl sulfide, diethyl sulfide, thiophene, tetrahydrothiophene, dimethyl sulfoxide, sulfolane, and the like.

The amount of the solvent used other than the polar protic solvent is preferably not larger than 4-fold by weight, more preferably not larger than 2-fold by weight, of epichlorohydrin.

As for the sequence and method of introducing the raw materials, a solution containing epichlorohydrin and the polar protic solvent may be added to 3,4'-diaminodiphenyl ether. Alternatively, epichlorohydrin or the solution containing epichlorohydrin and the polar protic solvent may be added to a solution containing 3,4'-diaminodiphenyl ether and the polar protic solvent. Conversely, the solution containing 3,4'-diaminodiphenyl ether and the polar protic solvent may be added to epichlorohydrin. Alternatively, 3,4'-diaminodiphenyl ether or a solution containing 3,4'-diaminodiphenyl ether and an alcohol may be added to the solution containing epichlorohydrin and the polar protic solvent.

In addition, the reaction temperature in the addition reaction step is 65 to 100° C., preferably 70 to 90° C. If the reaction temperature is lower than 65° C., it takes time to complete the reaction. Thus, such a temperature is economically disadvantageous. If the reaction temperature exceeds 100° C., N,N,N',N'-tetrakis(3-chloro-2-hydroxypropyl)-3,4'-diaminodiphenyl ether reacts with epichlorohydrin in the system due to excessive heat, and thereby impurities such as oligomer form are increased. Accordingly, the product purity is lowered, while the viscosity is increased.

The reaction period of the addition reaction is, under stirring after the addition of the raw materials is finished, 12 hours or longer, preferably 12 to 100 hours, and more preferably 12 to 50 hours. If the reaction period of the addition reaction is shorter than 12 hours, the reaction to form the tetrafunctional product of 3-chloro-2-hydroxypropyl proceeds incompletely, and an impurity content of diglycidyl and triglycidyl is increased after the production. As a result, the storage stability is significantly deteriorated. If the reaction period of the addition reaction is 100 hours or longer, N,N,N',N'-tetrakis(3-chloro-2-hydroxypropyl)-3,4'-diaminodiphenyl ether reacts with epichlorohydrin in the system. This increases impurities such as oligomer form, and lowers the product purity, while increasing the viscosity.

The time when the amount of remaining tri(chlorohydrin) form becomes the smallest indicates that the reaction in the addition reaction step is completed. In addition, after the addition reaction step is completed, and before the cyclization reaction step is started, at least a portion of the polar protic solvent and epichlorohydrin in the addition reaction step should be removed by an ordinally-employed method such as distillation, and the reaction liquid should be concentrated. The removal of the polar protic solvent and epichlorohydrin helps to increase the efficiency of water-washing and removing a salt generated by dehydrochlorination from a reaction solution after completion of the cyclization reaction step as described later. Further, at least the portion of the polar protic solvent and epichlorohydrin distilled off may be recycled in the addition reaction.

In the cyclization reaction step, N,N,N',N'-tetrakis(3-chloro-2-hydroxypropyl)-3,4'-diaminodiphenyl ether is reacted with an alkali compound for dehydrochlorination.

Examples of the alkali compound include lithium hydroxide, sodium hydroxide, potassium hydroxide, barium hydroxide, magnesium hydroxide, calcium hydroxide, lithium carbonate, sodium carbonate, potassium carbonate, barium carbonate, magnesium carbonate, calcium carbonate, lithium hydrogen carbonate, sodium hydrogen carbonate, potassium hydrogen carbonate, lithium hydride, sodium hydride, potassium hydride, sodium methoxide, potassium methoxide, sodium ethoxide, potassium ethoxide, sodium n-propoxide, potassium n-propoxide, sodium isopropoxide, potassium isopropoxide, sodium n-butoxide, potassium n-butoxide, sodium tert-butoxide, potassium tert-butoxide, sodium tert-amylate, potassium tert-amylate, sodium n-hexylate, potassium n-hexylate, tetramethylammonium hydroxide, and the like. Above all, sodium hydroxide and potassium hydroxide are preferably used. These alkali compounds may be introduced directly, or may be added dropwise in the form of an aqueous or alcohol solution.

The amount of the alkali compound used is preferably 4 to 16-fold by mole, more preferably 5 to 12-fold by mole, relative to one mole of 3,4'-diaminodiphenyl ether. If the amount of the alkali compound used is less than 4-fold by mole, the purity and yield of target N,N,N',N'-tetraglycidyl-3,4'-diaminodiphenyl ether are lowered. Meanwhile, if the amount of the alkali compound used exceeds 16-fold by mole, a large amount of energy is required to separate the target from the reaction liquid after the cyclization reaction step, and also a larger amount of waste is generated. Thus, such an amount is economically disadvantageous.

The cyclization reaction is preferably performed in the copresence of a quaternary ammonium salt and/or a quaternary phosphonium salt. The addition and copresence of these salts promote the cyclization reaction of the glycidyl group from the 3-chloro-2-hydroxypropyl group, improving the yield of the epoxy compound.

Examples of the quaternary ammonium salt include bromides, chlorides, iodides, hydrogen sulfates, hydroxides, and the like of tetramethyl ammonium, trimethyl-ethyl ammonium, dimethyl diethyl ammonium, triethyl-methyl ammonium, tripropyl-methyl ammonium, tributyl-methyl ammonium, trioctyl-methyl ammonium, tetraethyl ammonium, trimethyl-propyl ammonium, trimethyl phenyl ammonium, benzyl trimethyl ammonium, benzyl triethyl ammonium, diallyl dimethyl ammonium, n-octyl trimethyl ammonium, stearyl trimethyl ammonium, cetyl dimethyl ethyl ammonium, tetrapropyl ammonium, tetra n-butyl ammonium, β-methylcholine, tetra-n-butyl ammonium, phenyl trimethyl ammonium, and the like. Particularly preferable are bromides, chlorides, hydrogen sulfates, and hydroxides of trioctyl-methyl ammonium, tetraethyl ammonium, benzyl trimethyl ammonium, benzyl triethyl ammonium, and tetra n-butyl ammonium.

Further, examples of the quaternary phosphonium salt include bromides, chlorides, iodides, hydrogen sulfates, hydroxides, and the like of tetramethylphosphonium, trimethyl-ethyl-phosphonium, dimethyldiethylphosphonium, triethyl-methylphosphonium, tripropyl-methylphosphonium, tributyl-methylphosphonium, trioctyl-methylphosphonium, tetraethylphosphonium, trimethyl-propylphosphonium, trimethylphenylphosphonium, benzyltrimethylphosphonium, diallyldimethylphosphonium, n-octyltrimethylphosphonium, stearyltrimethylphosphonium, cetyldimethylethylphosphonium, tetrapropylphosphonium, tetra n-butylphosphonium, tetra-n-butylphosphonium, phenyltrimethylphosphonium, methyltriphenylphosphonium, ethyltriphenylphosphonium, tetraphenylphosphonium, and the like.

The amount of the quaternary ammonium salt and/or the quaternary phosphonium salt added may be the catalyst quantity, and preferably 0.001 to 0.5-fold by mole, more preferably 0.01 to 0.1-fold by mole, of 3,4'-diaminodiphenyl ether. When the amount of the quaternary ammonium salt and the quaternary phosphonium salt added is within such a range, the cyclization reaction of the glycidyl group from the 3-chloro-2-hydroxypropyl group is promoted, and thus the yield and the chemical purity can be increased.

The reaction temperature in the cyclization reaction step is preferably 0 to 90° C., more preferably 20 to 60° C. Moreover, the reaction period of the cyclization reaction step is, after the addition of the alkali compound is finished, preferably 0.5 to 10 hours, more preferably 1 to 6 hours.

As a solvent in the cyclization reaction step, any selected from an alcohol solvent, a hydrocarbon solvent, an ether solvent, and an ester solvent is preferably used.

Examples of the alcohol solvent in the cyclization reaction step include primary alcohols such as methanol, ethanol, 1-propanol, 1-butanol, 1-pentanol and 1-hexanol; secondary alcohols such as isopropanol, 2-butanol, 2-pentanol, 3-pentanol, 2-hexanol, cyclohexanol, 2-heptanol and 3-heptanol; tert-butanol, tert-pentanol, ethylene glycol, ethylene glycol monomethyl ether, ethylene glycol monoethyl ether, ethylene glycol mono-n-propyl ether, ethylene glycol mono-n-butyl ether, ethylene glycol monophenyl ether, diethylene glycol, diethylene glycol monomethyl ether, diethylene glycol monoethyl ether, diethylene glycol mono-n-propyl ether, diethylene glycol mono-n-butyl ether, triethylene glycol, triethylene glycol monomethyl ether, triethylene glycol mono-n-butyl ether, propylene glycol, propylene glycol monomethyl ether, propylene glycol monoethyl ether, propylene glycol mono-n-propyl ether, propylene glycol mono-n-butyl ether, propylene glycol monophenyl ether, dipropylene glycol, dipropylene glycol monomethyl ether, dipropylene glycol monoethyl ether, dipropylene glycol mono-n-propyl ether, dipropylene glycol mono-n-butyl ether, tripropylene glycol, tripropylene glycol monomethyl ether, and tripropylene glycol mono-n-butyl ether.

Examples of the hydrocarbon solvent include hexane, 2-methylpentane, 2,2-dimethylbutane, 2,3-dimethylbutane, heptane, octane, isooctane, nonane, trimethylhexane, decane, dodecane, benzene, toluene, xylene, ethylbenzene, cumene, mesitylene, cyclohexylbenzene, diethylbenzene, cyclopentane, methylcyclopentane, cyclohexane, methylcyclohexane, ethylcyclohexane, and the like.

Moreover, examples of the ether solvent include diisopropyl ether, dibutyl ether, dihexyl ether, anisole, phenetole, diphenyl ether, tetrahydrofuran, tetrahydropyran, ethylene glycol dibutyl ether, diethylene glycol dimethyl ether, diethylene glycol diethyl ether, diethylene glycol dibutyl ether, and the like.

Additionally, examples of the ester solvent include methyl acetate, ethyl acetate, propyl acetate, isopropyl acetate, butyl acetate, isobutyl acetate, and the like.

Above all, solvents preferably used in the cyclization reaction step are methanol, ethanol, 1-propanol, 1-butanol, isopropanol, 2-butanol, tert-butanol, cyclohexane, toluene, xylene, ethylbenzene, cumene, mesitylene, and diethylbenzene.

The amount of the solvent used in the cyclization reaction step is preferably 1 to 20-fold by weight, more preferably 2 to 10-fold by weight, of 3,4'-diaminodiphenyl ether. When the amount of the solvent used in the cyclization reaction step is within such a range, the viscosity of the reaction liquid is lowered, making the mixing state favorable. Thus, the reaction proceeds rapidly.

The reaction solution obtained in the aforementioned cyclization reaction step contains N,N,N',N'-tetraglycidyl-3,4'-diaminodiphenyl ether, a salt generated by the dehydrochlorination, and the solvent. The reaction solution has a low content of impurities such as diglycidyl, triglycidyl, and chlorohydroxypropyl forms. Thus, by removing only the salt and the solvent from the reaction liquid, N,N,N',N'-tetraglycidyl-3,4'-diaminodiphenyl ether having a high chemical purity and a low viscosity can be obtained.

The salt generated by the dehydrochlorination can be dissolved and removed by washing with water. Furthermore, the solvent can be removed by separating and removing an aqueous layer from the washed reaction liquid, and by subjecting a resultant oil layer to distillation by heating under reduced pressure.

High-purity N,N,N',N'-tetraglycidyl-3,4'-diaminodiphenyl ether obtained in this manner is preferably used in a variety of industrial applications, such as fine chemicals, raw materials of drugs and agrochemicals, a sealing material of electrical and electronic components, electronic information materials, optical materials, insulating materials, adhesives, and raw materials of resins forming, for example, composite materials with glass fibers, carbon fibers, and the like. Above all, preferable applications are a sealing material of electrical and electronic components, insulating materials, adhesives, and composite materials with glass fibers, carbon fibers, and the like.

A highly-functional epoxy resin-cured product having high strength, high elasticity, high adhesiveness, high toughness, heat resistance, weather resistance, solvent resistance, impact resistance, and the like, can be obtained by impregnating a glass fiber, a carbon fiber, or the like with a resin composition containing high-purity N,N,N',N'-tetraglycidyl-3,4'-diaminodiphenyl ether and a hardener, followed by curing. Moreover, a cured product usable in, for example, adhesives, paints, and the like, can be obtained by mixing high-purity N,N,N',N'-tetraglycidyl-3,4'-diaminodiphenyl ether with an ordinary epoxy resin, followed by curing with an amine. These cured products are cured products having high mechanical properties and electrical properties and also having high durability and reliability.

High-purity N,N,N',N'-tetraglycidyl-3,4'-diaminodiphenyl ether obtained has a high chemical purity of 85% or higher, a low viscosity at 40° C. of 40 Pa·s or lower, and a low content of impurities such as diglycidyl, triglycidyl, and chlorohydroxypropyl forms, and accordingly is excellent in storage stability. A product using this compound has quite excellent durability and reliability.

EXAMPLES

Hereinafter, description will be specifically given based on Examples. However, this disclosure is not limited only to Examples. Note that, in Examples and Comparative Examples below, the phrase "oo-fold by weight/3,4'-diaminodiphenyl ether" means each additive amount is oo-fold by weight of 3,4'-diaminodiphenyl ether.

Example 1

Into a four-neck flask equipped with a thermometer, a condenser and a stirrer, 1500 g (16.2 mol) of epichlorohydrin and 675 g (2.5-fold by weight/3,4'-diaminodiphenyl ether) of 2-propanol were introduced, to which 270 g (1.35 mol) of 3,4'-diaminodiphenyl ether was added. This liquid mixture was stirred at a temperature of 80° C. for 21 hours to carry out an addition reaction. From the addition reaction solution, a portion, 1178 g, of 2-propanol and remaining epichlorohydrin were distilled off under reduced pressure. To the resultant concentrate, 540 g (2.0-fold by weight/3,4'-diaminodiphenyl ether) of toluene and 13.8 g (0.041 mol) of tetrabutylammonium hydrogen sulfate serving as a catalyst of a cyclization reaction were added. Subsequently, 675 g (8.1 mol) of 48% sodium hydroxide was added dropwise thereto at a temperature of 30° C. for 30 minutes. With further stirring at a temperature of 30° C. for 4 hours for maturation, the cyclization reaction was then carried out. After completion of the cyclization reaction, a salt thus generated was dissolved in 810 g (3.0-fold by weight/3,4'-diaminodiphenyl ether) of water, and an aqueous layer and an oil layer were separated. The oil layer was further washed with 810 g (3.0-fold by weight/3,4'-diaminodiphenyl ether) of water, and an aqueous layer and an oil layer were separated. After toluene and epichlorohydrin were distilled off from the oil layer under reduced pressure, a brown viscous liquid mainly containing N,N,N',N'-tetraglycidyl-3,4'-diaminodiphenyl ether was obtained. The yield of this epoxy compound was 573 g (100% of the theoretical yield). Moreover, the chemical purity of the epoxy compound measured by the aforementioned method using high-performance liquid chromatography (hereinafter, referred to as "HPLC") was 87% (HPLC area %). Further, the epoxy equivalent weight was 122 g/eq, and the viscosity measured at 40° C. using an E-type viscometer was 36 Pa·s.

Example 2

The same procedure was performed as in Example 1, except that 2-propanol in Example 1 was changed to 675 g (2.5-fold by weight/3,4'-diaminodiphenyl ether) of ethanol. Thus, 575 g of a brown viscous liquid mainly containing N,N,N',N-tetraglycidyl-3,4'-diaminodiphenyl ether was obtained (100% of the theoretical yield). The chemical purity of this epoxy compound measured by the aforementioned method using HPLC was 87% (HPLC area %). The epoxy equivalent weight was 123 g/eq, and the viscosity measured at 40° C. using the E-type viscometer was 35 Pa·s.

Example 3

The same procedure was performed as in Example 1, except that the amount of 2-propanol serving as the addition reaction solvent was changed from 675 g in Example 1 to 1080 g (4.0-fold by weight/3,4'-diaminodiphenyl ether), that the reaction period of the addition reaction was changed from 21 hours to 25 hours, and that the amount of 2-propanol and remaining epichlorohydrin distilled off from the addition reaction solution was changed to 1620 g. Thus, 565 g of a brown viscous liquid mainly containing N,N,N',N'-tetraglycidyl-3,4'-diaminodiphenyl ether was obtained (99% of the theoretical yield). The chemical purity of this epoxy compound measured by the aforementioned method using HPLC was 91% (HPLC area %). The epoxy equivalent weight was 119 g/eq, and the viscosity measured at 40° C. using the E-type viscometer was 29 Pa·s.

Example 4

The same procedure was performed as in Example 1, except that the reaction period of the addition reaction was changed from 21 hours in Example 1 to 15 hours. Thus, 568 g of a brown viscous liquid mainly containing N,N,N',N'-tetraglycidyl-3,4'-diaminodiphenyl ether was obtained (99% of the theoretical yield). The chemical purity of this epoxy compound measured by the aforementioned method using HPLC was 86% (HPLC area %). The epoxy equivalent weight was 126 g/eq, and the viscosity measured at 40° C. using the E-type viscometer was 39 Pa·s.

Example 5

The same procedure was performed as in Example 1, except that the reaction temperature of the addition reaction was changed from 80° C. in Example 1 to 70° C., and that the reaction period was changed from 21 hours to 28 hours. Thus, 569 g of a brown viscous liquid mainly containing N,N,N',N'-tetraglycidyl-3,4'-diaminodiphenyl ether was obtained (99% of the theoretical yield). The chemical purity of this epoxy compound measured by the aforementioned method using HPLC was 93% (HPLC area %). The epoxy equivalent weight was 119 g/eq, and the viscosity measured at 40° C. using the E-type viscometer was 29 Pa·s.

Example 6

The same procedure was performed as in Example 3, except that the reaction temperature of the addition reaction was changed from 80° C. in Example 3 to 70° C., and that the reaction period was changed from 25 hours to 35 hours. Thus, 567 g of a brown viscous liquid mainly containing N,N,N',N'-tetraglycidyl-3,4'-diaminodiphenyl ether was obtained (99% of the theoretical yield). The chemical purity of this epoxy compound measured by the aforementioned method using HPLC was 92% (HPLC area %). The epoxy equivalent weight was 119 g/eq, and the viscosity measured at 40° C. using the E-type viscometer was 27 Pa·s.

Example 7

The same procedure was performed as in Example 1, except that the cyclization reaction catalyst was changed from 13.8 g (0.041 mol) of tetrabutylammonium hydrogen sulfate in Example 1 to 15.2 g (0.041 mol) of ethyltriphenylphosphonium bromide. Thus, 576 g of a brown viscous liquid mainly containing N,N,N',N'-tetraglycidyl-3,4'-diaminodiphenyl ether was obtained (101% of the theoretical yield). The chemical purity of this epoxy compound measured by the aforementioned method using HPLC was 87% (HPLC area %). The epoxy equivalent weight was 123 g/eq, and the viscosity measured at 40° C. using the E-type viscometer was 36 Pa·s.

Example 8

The same procedure was performed as in Example 1, except that no cyclization reaction catalyst was used, and that the cyclization reaction solvent was changed from toluene in Example 1 to 540 g (2.0-fold by weight/3,4'-diaminodiphenyl ether) of 2-propanol. Thus, 567 g of a brown viscous liquid mainly containing N,N,N',N'-tetraglycidyl-3,4'-diaminodiphenyl ether was obtained (99% of the theoretical yield). The chemical purity of this epoxy compound measured by the aforementioned method using HPLC was 86% (HPLC area %). The epoxy equivalent weight was 124 g/eq, and the viscosity measured at 40° C. using the E-type viscometer was 37 Pa·s.

Example 9

Into a 500-L reaction vessel equipped with a thermometer, a condenser and a stirrer, 250 kg (2.7 kmol) of epichlorohydrin and 180 kg (4.0-fold by weight/3,4'-diaminodiphenyl ether) of 2-propanol were introduced, to which 45 kg (0.225 kmol) of 3,4'-diaminodiphenyl ether was added. This liquid mixture was stirred at a temperature of 80° C. for 25 hours to carry out an addition reaction. From the addition reaction solution, a portion, 269 kg, of 2-propanol and remaining epichlorohydrin were distilled off under reduced pressure. To the concentrate, 90 kg (2.0-fold by weight/3,4'-diaminodiphenyl ether) of toluene and 2.3 kg (6.8 kmol) of tetrabutylammonium hydrogen sulfate serving as a catalyst of a cyclization reaction were added. Subsequently, 112 kg (1.34 kmol) of an aqueous solution of 48% sodium hydroxide was added dropwise thereto at a temperature of 30° C. for 1 hour. With further stirring at a temperature of 30° C. for 4 hours for maturation, the cyclization reaction was then carried out. After completion of the cyclization reaction, a salt thus generated was dissolved in 135 kg (3.0-fold by weight/3,4'-diaminodiphenyl ether) of water, and an aqueous layer and an oil layer were separated. The oil layer was further washed with 135 kg (3.0-fold by weight/3,4'-diaminodiphenyl ether) of water, and an aqueous layer and an oil layer were separated. After toluene and epichlorohydrin were distilled off from the oil layer under reduced pressure, a brown viscous liquid mainly containing N,N,N',N'-tetraglycidyl-3,4'-diaminodiphenyl ether was obtained. The yield of this epoxy compound was 94 kg (98% of the theoretical yield). Moreover, the chemical purity of the epoxy compound measured by the aforementioned method using HPLC was 90% (HPLC area %). The epoxy equivalent weight was 121 g/eq, and the viscosity measured at 40° C. using the E-type viscometer was 29 Pa·s.

Example 10

The same procedure was performed as in Example 1, except that the addition reaction solvent was changed from 675 g of 2-propanol in Example 1 to 67.5 g (0.25-fold by weight/3,4'-diaminodiphenyl ether) of water. Thus, 540 g of a brown viscous liquid mainly containing N,N,N',N'-tetraglycidyl-3,4'-diaminodiphenyl ether was obtained (94% of the theoretical yield). The chemical purity of this epoxy compound measured by the aforementioned method using HPLC was 85% (HPLC area %). The epoxy equivalent weight was 124 g/eq, and the viscosity measured at 40° C. using the E-type viscometer was 39 Pa·s.

Example 11

The same procedure was performed as in Example 10, except that the addition reaction solvent was changed from 67.5 g of water in Example 10 to a solvent mixture including 675 g (2.5-fold by weight/3,4'-diaminodiphenyl ether) of toluene and 67.5 g (0.25-fold by weight/3,4'-diaminodiphenyl ether) of water. Thus, 572 g of a brown viscous liquid mainly containing N,N,N',N'-tetraglycidyl-3,4'-diaminodiphenyl ether was obtained (100% of the theoretical yield). The chemical purity of this epoxy compound measured by the aforementioned method using HPLC was 90% (HPLC area %). The epoxy equivalent weight was 118 g/eq, and the viscosity measured at 40° C. using the E-type viscometer was 28 Pa·s.

Comparative Example 1

The same procedure was performed as in Example 1, except that the addition reaction solvent was changed from 2-propanol in Example 1 to 675 g (2.5-fold by weight/3,4'-diaminodiphenyl ether) of N,N-dimethylformamide. Thus, 491 g of a brown viscous liquid was obtained (86% of the theoretical yield). The chemical purity of this epoxy compound was measured by the aforementioned method using HPLC, and N,N,N',N'-tetraglycidyl-3,4'-diaminodiphenyl ether had a purity of 27% (HPLC area %). The epoxy equivalent weight was 419 g/eq, and the viscosity measured at 40° C. using the E-type viscometer exceeded 100 Pa·s and was unmeasurable.

Comparative Example 2

The same procedure was performed as in Example 1, except that the addition reaction solvent was changed from 2-propanol in Example 1 to 675 g (2.5-fold by weight/3,4'-diaminodiphenyl ether) of 1,4-dioxane. Thus, 544 g of a brown viscous liquid mainly containing N,N,N',N'-tetraglycidyl-3,4'-diaminodiphenyl ether was obtained (95% of the theoretical yield). The chemical purity of this epoxy compound measured by the aforementioned method using HPLC was 70% (HPLC area %). The epoxy equivalent weight was 125 g/eq, and the viscosity measured at 40° C. using the E-type viscometer was 48 Pa·s.

Comparative Example 3

The same procedure was performed as in Example 1, except that the addition reaction solvent was changed from 2-propanol in Example 1 to 675 g (2.5-fold by weight/3,4'-diaminodiphenyl ether) of ethyl acetate. Thus, 561 g of a brown viscous liquid mainly containing N,N,N',N'-tetraglycidyl-3,4'-diaminodiphenyl ether was obtained (98% of the theoretical yield). The chemical purity of this epoxy compound measured by the aforementioned method using HPLC was 81% (HPLC area %). The epoxy equivalent weight was 124 g/eq, and the viscosity measured at 40° C. using the E-type viscometer was 46 Pa·s.

Comparative Example 4

The same procedure was performed as in Example 1, except that the addition reaction solvent was changed from 2-propanol in Example 1 to 675 g (2.5-fold by weight/3,4'-diaminodiphenyl ether) of 2-butanone. Thus, 569 g of a brown viscous liquid mainly containing N,N,N',N'-tetraglycidyl-3,4'-diaminodiphenyl ether was obtained (99% of the theoretical yield). The chemical purity of this epoxy compound measured by the aforementioned method using HPLC was 76% (HPLC area %). The epoxy equivalent weight was 134 g/eq, and the viscosity measured at 40° C. using the E-type viscometer was 53 Pa·s.

Comparative Example 5

The same procedure was performed as in Example 1, except that the addition reaction solvent was changed from 2-propanol in Example 1 to 1080 g (4.0-fold by weight/3,4'-diaminodiphenyl ether) of toluene. Thus, 560 g of a brown viscous liquid mainly containing N,N,N',N'-tetraglycidyl-3,4'-diaminodiphenyl ether was obtained (98% of the theoretical yield). The chemical purity of this epoxy compound measured by the aforementioned method using HPLC was 78% (HPLC area %). The epoxy equivalent weight was 125 g/eq, and the viscosity measured at 40° C. using the E-type viscometer was 45 Pa·s.

Comparative Example 6

The same procedure was performed as in Example 1, except that no addition reaction solvent was added, and that the amount of epichlorohydrin introduced was changed from 1500 g in Example 1 to 2875 g (31.1 mol). Thus, 551 g of a brown viscous liquid mainly containing N,N,N',N'-tetraglycidyl-3,4'-diaminodiphenyl ether was obtained (96% of the theoretical yield). The chemical purity of this epoxy compound measured by the aforementioned method using HPLC was 79% (HPLC area %). The epoxy equivalent weight was 129 g/eq, and the viscosity measured at 40° C. using the E-type viscometer was 68 Pa·s.

Comparative Example 7

The same procedure was performed as in Example 1, except that the reaction period of the addition reaction was changed from 21 hours in Example 1 to 10 hours. Thus, 578 g of a brown viscous liquid mainly containing N,N,N',N'-tetraglycidyl-3,4'-diaminodiphenyl ether was obtained (101% of the theoretical yield). The chemical purity of this epoxy compound measured by the aforementioned method using HPLC was 83% (HPLC area %). The epoxy equivalent weight was 126 g/eq, and the viscosity measured at 40° C. using the E-type viscometer was 44 Pa·s.

Comparative Example 8

The same procedure was performed as in Example 1, except that the reaction temperature of the addition reaction was changed from 80° C. in Example 1 to 60° C. Thus, 544 g of a brown viscous liquid mainly containing N,N,N',N'-tetraglycidyl-3,4'-diaminodiphenyl ether was obtained (95% of the theoretical yield). The chemical purity of this epoxy compound measured by the aforementioned method using HPLC was 75% (HPLC area %). The epoxy equivalent weight was 119 g/eq, and the viscosity measured at 40° C. using the E-type viscometer was 25 Pa·s.

Comparative Example 9

The same procedure was performed as in Example 11, except that the addition reaction solvent was changed from the solvent mixture including 675 g of toluene and 67.5 g of water in Example 11 to a solvent mixture including 675 g of toluene and 67.5 g (0.25-fold by weight/3,4'-diaminodiphenyl ether) of acetic acid. Thus, 583 g of a brown viscous liquid mainly containing N,N,N',N'-tetraglycidyl-3,4'-diaminodiphenyl ether was obtained (102% of the theoretical yield). The chemical purity of this epoxy compound measured by the aforementioned method using HPLC was 75% (HPLC area %). The epoxy equivalent weight was 140 g/eq, and the viscosity measured at 40° C. using the E-type viscometer exceeded 100 Pa·s and was unmeasurable.

Tables 1 to 3 show the reaction conditions and the qualities of N,N,N',N'-tetraglycidyl-3,4'-diaminodiphenyl ether of Examples and Comparative Examples.

TABLE 1

| | | | Example 1 | Example 2 | Example 3 | Example 4 | Example 5 | Example 6 |
|---|---|---|---|---|---|---|---|---|
| Addition reaction conditions | Amount of 3,4'-diaminodiphenyl ether used | Mole | 1.35 | 1.35 | 1.35 | 1.35 | 1.35 | 1.35 |
| | Amount of epichlorohydrin used | Fold by mole | 12 | 12 | 12 | 12 | 12 | 12 |
| | Polar protic solvent | Solvent species | IPA | Ethanol | IPA | IPA | IPA | IPA |
| | | Fold by weight | 2.5 | 2.5 | 4.0 | 2.5 | 2.5 | 4.0 |
| | Reaction temperature | ° C. | 80 | 80 | 80 | 80 | 70 | 70 |
| | Reaction period | h | 21 | 21 | 25 | 15 | 28 | 35 |
| Cyclization reaction conditions | Solvent species | — | Toluene | Toluene | Toluene | Toluene | Toluene | Toluene |
| | Solvent amount | Fold by weight | 2.0 | 2.0 | 2.0 | 2.0 | 2.0 | 2.0 |
| | Catalyst species | — | TBAHS | TBAHS | TBAHS | TBAHS | TBAHS | TBAHS |
| | Catalyst amount | Fold by mole | 0.03 | 0.03 | 0.03 | 0.03 | 0.03 | 0.03 |
| Product qualities | Chemical purity | HPLC area % | 87 | 87 | 91 | 86 | 93 | 92 |
| | Epoxy equivalent weight | g/eq | 122 | 123 | 119 | 126 | 119 | 119 |
| | Viscosity (E-type, 40° C.) | Pa·s | 36 | 35 | 29 | 39 | 29 | 27 |

In the table 1, fold by mole refers to a molar ratio relative to 3,4'-diaminodiphenyl ether, and fold by weight indicates a weight ratio relative to 3,4'-diaminodiphenyl ether. In addition, IPA represents 2-propanol, and TBAHS represents tetrabutylammonium hydrogen sulfate.

TABLE 2

| | | | Example 7 | Example 8 | Example 9 | Example 10 | Example 11 | Comparative Example 1 | Comparative Example 2 |
|---|---|---|---|---|---|---|---|---|---|
| Addition reaction conditions | Amount of 3,4'-diaminodiphenyl ether used | Mole | 1.35 | 1.35 | 225 | 1.35 | 1.35 | 1.35 | 1.35 |
| | Amount of epichlorohydrin used | Fold by mole | 12 | 12 | 12 | 12 | 12 | 12 | 12 |
| | Polar protic solvent | Solvent species | IPA | IPA | IPA | Water | Water | — | — |
| | | Fold by weight | 2.5 | 2.5 | 4.0 | 0.25 | 0.25 | — | — |

TABLE 2-continued

|  |  |  | Example 7 | Example 8 | Example 9 | Example 10 | Example 11 | Comparative Example 1 | Comparative Example 2 |
|---|---|---|---|---|---|---|---|---|---|
|  | Solvent other than polar protic solvent | Solvent species | — | — | — | — | Toluene | DMF | 1,4-dioxane |
|  |  | Fold by weight | — | — | — | — | 2.5 | 2.5 | 2.5 |
|  | Reaction temperature | °C. | 80 | 80 | 80 | 80 | 80 | 80 | 80 |
|  | Reaction period | H | 21 | 21 | 25 | 15 | 15 | 21 | 21 |
| Cyclization reaction conditions | Solvent species | — | Toluene | IPA | Toluene | Toluene | Toluene | Toluene | Toluene |
|  | Solvent amount | Fold by weight | 2.0 | 2.0 | 2.0 | 2.0 | 2.0 | 2.0 | 2.0 |
|  | Catalyst species | — | EtPh3PBr | None | TBAHS | TBAHS | TBAHS | TBAHS | TBAHS |
|  | Catalyst amount | Fold by mole | 0.03 | — | 0.03 | 0.03 | 0.03 | 0.03 | 0.03 |
| Product qualities | Chemical purity | HPLC area % | 87 | 86 | 90 | 85 | 90 | 27 | 70 |
|  | Epoxy equivalent weight | g/eq | 123 | 124 | 121 | 124 | 118 | 419 | 125 |
|  | Viscosity (E-type, 40° C.) | Pa·s | 36 | 37 | 29 | 39 | 28 | >100 | 48 |

In the table 2, fold by mole indicates a molar ratio relative to 3,4'-diaminodiphenyl ether, and fold by weight indicates a weight ratio relative to 3,4'-diaminodiphenyl ether. In addition, IPA represents 2-propanol, DMF represents N,N-dimethylformamide, TBAHS represents tetrabutylammonium hydrogen sulfate, and EtPh3PBr represents ethyltriphenylphosphonium bromide.

TABLE 3

|  |  |  | Comparative Example 3 | Comparative Example 4 | Comparative Example 5 | Comparative Example 6 | Comparative Example 7 | Comparative Example 8 | Comparative Example 9 |
|---|---|---|---|---|---|---|---|---|---|
| Addition reaction conditions | Amount of 3,4'-diaminodiphenyl ether used | Mole | 1.35 | 1.35 | 1.35 | 1.35 | 1.35 | 1.35 | 1.35 |
|  | Amount of epichlorohydrin used | Fold by mole | 12 | 12 | 12 | 23 | 12 | 12 | 12 |
|  | Polar protic solvent | Solvent species | — | — | — | — | IPA | IPA | Acetic acid |
|  |  | Fold by weight | — | — | — | — | 2.5 | 2.5 | 0.25 |
|  | Solvent other than polar protic solvent | Solvent species | Ethyl acetate | 2-butanone | Toluene | — | — | — | Toluene |
|  |  | Fold by weight | 2.5 | 2.5 | 4.0 | — | — | — | 2.5 |
|  | Reaction temperature | °C. | 80 | 80 | 80 | 80 | 80 | 60 | 80 |
|  | Reaction period | H | 21 | 21 | 21 | 21 | 10 | 21 | 15 |
| Cyclization reaction conditions | Solvent species | — | Toluene | Toluene | Toluene | Toluene | Toluene | Toluene | Toluene |
|  | Solvent amount | Fold by weight | 2.0 | 2.0 | 2.0 | 2.0 | 2.0 | 2.0 | 2.0 |
|  | Catalyst species | — | TBAHS | TBAHS | TBAHS | TBAHS | TBAHS | TBAHS | TBAHS |
|  | Catalyst amount | Fold by mole | 0.03 | 0.03 | 0.03 | 0.03 | 0.03 | 0.03 | 0.03 |
| Product qualities | Chemical purity | HPLC area % | 81 | 76 | 78 | 79 | 83 | 75 | 75 |
|  | Epoxy equivalent weight | g/eq | 124 | 134 | 125 | 129 | 126 | 119 | 140 |
|  | Viscosity (E-type, 40° C.) | Pa·s | 46 | 53 | 45 | 68 | 44 | 25 | >100 |

In the table 3, fold by mole indicates a molar ratio relative to 3,4'-diaminodiphenyl ether, and fold by weight indicates a weight ratio relative to 3,4'-diaminodiphenyl ether. In addition, IPA represents 2-propanol, and TBAHS represents tetrabutylammonium hydrogen sulfate.

In Tables 1 to 3, fold by mole in the columns of the amount of epichlorohydrin used and the catalyst amount indicates a molar ratio relative to 3,4'-diaminodiphenyl ether. Moreover, fold by weight in the columns of the polar protic solvent, the solvent other than the polar protic solvent, and the solvent amount in the cyclization reaction indicates a weight ratio relative to 3,4'-diaminodiphenyl ether. In addition, IPA represents 2-propanol, DMF represents N,N-dimethylformamide, TBAHS represents tetrabutylammonium hydrogen sulfate, and EtPh3PBr represents ethyltriphenylphosphonium bromide.

The invention claimed is:

1. A high-purity epoxy compound of N,N,N',N'-tetraglycidyl-3,4'-diaminodiphenyl ether having a chemical purity of 85% or higher and a viscosity at 40° C. of 40 Pa·s or lower measured using an E-type viscometer.

* * * * *